US012472283B2

(12) United States Patent
Pulgar

(10) Patent No.: US 12,472,283 B2
(45) Date of Patent: Nov. 18, 2025

(54) METHOD OF PERFORMING A BUTTOCKS AND HIP AUGMENTATION USING PLASMA GEL

(71) Applicant: Johanna Andrea Pulgar, Miami, FL (US)

(72) Inventor: Johanna Andrea Pulgar, Miami, FL (US)

( * ) Notice: Subject to any disclaimer, the term of this patent is extended or adjusted under 35 U.S.C. 154(b) by 621 days.

(21) Appl. No.: 17/959,419

(22) Filed: Oct. 4, 2022

(65) Prior Publication Data

US 2024/0108788 A1 Apr. 4, 2024

(51) Int. Cl.
*A61L 27/36* (2006.01)
*A61F 2/02* (2006.01)

(52) U.S. Cl.
CPC ............ *A61L 27/3616* (2013.01); *A61F 2/02* (2013.01); *A61L 27/3641* (2013.01); *A61L 27/3691* (2013.01); *A61F 2210/0061* (2013.01); *A61L 2400/06* (2013.01)

(58) Field of Classification Search
None
See application file for complete search history.

(56) References Cited

U.S. PATENT DOCUMENTS 9,199,007 B2 * 12/2015 Julián Ibáñez ....... A61L 27/227

FOREIGN PATENT DOCUMENTS

UA 133190 U * 3/2019 ......... A61L 27/3616

* cited by examiner

*Primary Examiner* — David H Willse
(74) *Attorney, Agent, or Firm* — Ruben Alcoba, Esq.

(57) ABSTRACT

A method of performing a buttocks and hip augmentation using plasma gel. The method begins by extracting at least 340 ml of blood from a patient. Then, separating the liquid plasma from the blood of the patient. Next, transforming the liquid blood into a plasma gel. Then, marking an area of the buttocks or hips of the patient that will receive the plasma gel for augmentation. Next, injecting the plasma gel into the areas that are to be augmented until augmentation is reached. Lastly, covering the injection point that was used to create the augmentation.

8 Claims, 4 Drawing Sheets

METHOD OF PERFORMING A BUTTOCKS AND HIP AUGMENTATION USING PLASMA GEL

BACKGROUND

The present invention is a method of performing a buttocks and hip augmentation using plasma gel.

The present invention was conceived when a patient of the inventor asked her if there was any way of increasing one's own buttocks or hips without having to use implants.

The inventor, being a medical doctor, investigated methods of how to augment one's body naturally and realized that patients' faces were being augmented using plasma gel.

She looked into how the faces were being augmented and realized that the method that was used to augment faces was not feasible if one wished to augment one's own buttocks and hips.

The reason being that the needles and blood extraction, equipment used to perform the face augmentations were not suitable for buttocks and hip augmentations.

She also realized that to use plasma gel in the buttocks and hips of a patient that she had to map and mark areas of the buttocks and hips that needed to be augmented in a least intrusive manner.

Based on her research, the inventor realized that there were four points of needle insertion that would allow her to minimize the intrusions into the buttocks and hips of the patient.

The four points are shown in FIGS. 1-4 of the present application. The Figs. also show the preferred method of directing the needle that will distribute the plasma gel within the adipose tissue of the patient.

The present invention eliminates the need of using prosthetics to augment one's buttocks or hips.

SUMMARY

The present invention is a method of performing a buttocks and hip augmentation using plasma gel. The method begins by extracting at least 340 ml of blood from a patient. Then, separating the liquid plasma from the blood of the patient. Next, transforming the liquid blood into a plasma gel. Then, marking an area of the buttocks or hips of the patient that will receive the plasma gel for augmentation. Next, injecting the plasma gel into the areas that are to be augmented until augmentation is reached. Lastly, covering the injection point that was used to create the augmentation.

An object of the present invention is to provide a method that will use one's own plasma to augment one's own buttocks and hip.

Another object of the present invention is to use a minimal amount of blood collection tubes when performing a plasma gel buttocks and hip augmentation.

Yet another object of the present invention is to reduce the time needed to collect blood and transform the blood into a plasma gel that can be used to perform a plasma gel buttocks and hip augmentation.

Still another object of the present invention is to eliminate the use of a girdle that a patient normally wears when a buttocks or hip augmentation is made.

BRIEF DESCRIPTION OF THE DRAWINGS

These and other features, aspects, and advantages of the present invention will become better understood with regards to the following description, appended claims, and drawings where:

DESCRIPTION

Figure 1:
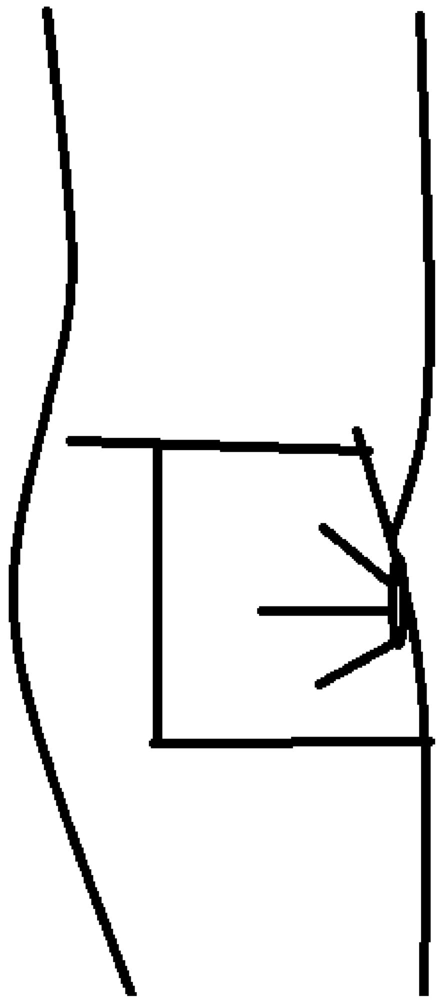
FIG. 1 shows a side view rendering of a patient's body wherein a plasma gel injection would be inserted to increase the hips of the patient.
Figure 2:
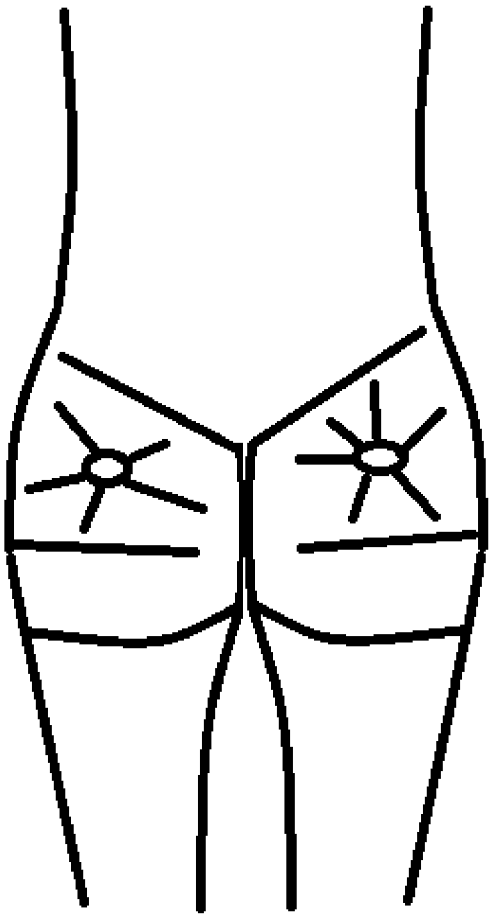
FIG. 2 shows a rear-view rendering of a patient's body wherein a plasma gel injection would be inserted to increase the volume of the upper part of the buttocks.
Figure 3:
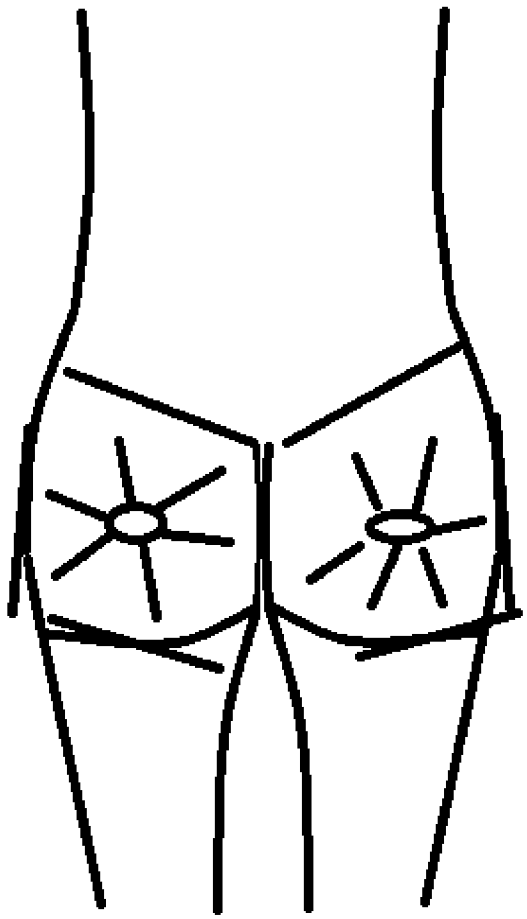
FIG. 3 shows a rear-view rendering of a patient's body wherein a plasma gel injection would be inserted to increase the volume of the buttocks.
Figure 4:
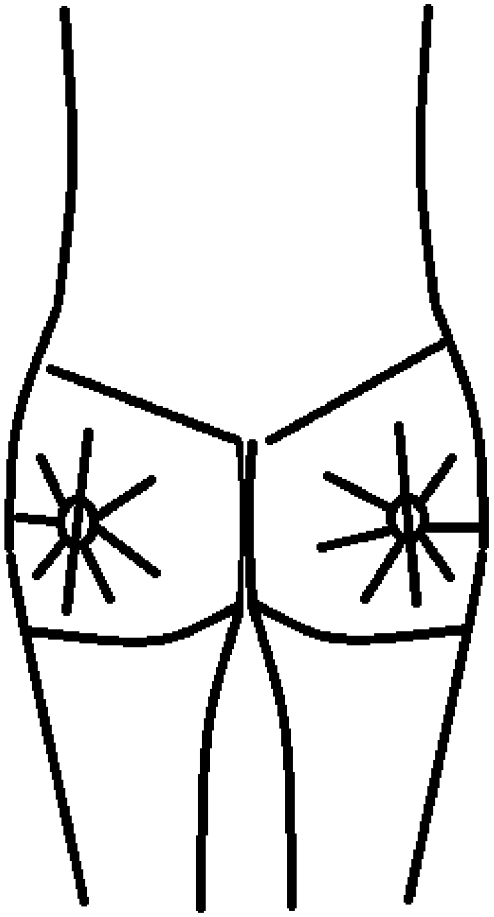
FIG. 4 shows a rear-view rendering of a patient's body wherein a plasma gel injection would be inserted to increase the volume of the side section of the buttocks.

The present invention is a method of performing a buttocks and hip augmentation using plasma gel. The method comprises providing at least thirty-six 8.5 ml blood collection tubes, a 21-gauge butterfly needle, a plurality of 10 ml syringes and a plurality of caps for the plurality of 10 ml syringes, a centrifuge, a heating machine that is configured to receive the plurality of 10 ml syringes, a container that holds cold water, a pair of 10 ml syringes, the pair of 10 ml syringes are filled with 6 ml of a solution that comprises of a lidocaine and of a 2 percent epinephrine, the solution hereinafter shall be referred as an anesthetic, an 18-gauge needle, a marker that is configured to mark an area of a patient wherein a plasma gel will be injected, a sterilizing solution that is used to sterilize a skin of the patient that will receive a treatment, a disposable sterilized undergarment that will cover an area of the patient that will receive the treatment, a band-aid, the patient, and a bed wherein the patient shall rest. The method begins by extracting blood from the patient into the at least thirty-six 8.5 ml blood collection tubes using the 21-gauge butterfly needle, thereby creating at least thirty-six blood filled collection tubes. Then, placing the at least thirty-six blood filled collection tubes into the centrifuge for a period of at least ten minutes. Next, extracting from the at least thirty-six blood filled collection tubes a liquid plasma using the plurality of 10 ml syringes and capping the syringes with the plurality of caps, thereby creating a plurality of liquid plasma filled and capped 10 ml syringes. Then, placing the plurality of liquid plasma filled and capped 10 ml syringes into a plated rich plasma heating machine for at least 3 minutes, therefore transforming the liquid plasma into a plasma gel, and thereby creating a plurality of plasma gel filled 10 ml syringes. Next, cooling the plasma gel of the plurality of plasma gel filled 10 ml syringes in the container that holds the cold water for a period of at least 5 minutes. Then, instructing the patient to put on the disposable sterilized undergarment. Next, having the patient rest on the platform so that the area of the patient that will receive a treatment is exposed, the area of the patient that will receive treatment shall either be a buttocks or a hip of the patient. Then, marking with the marker the area of the patient wherein the 18-gauge needle will be inserted, the marking shall comprise of a plurality of directional lines that will flow outward from an insertion point, the directional lines are configured to be used as a guide as to the direction in which the plasma gel is to be injected. Then, sterilizing the area of the patient that will receive treatment with a sterilizing solution. Next, inserting the 18-gauge needle into the insertion point. Then, connecting a 10 ml syringe of the pair of 10 ml syringes that contain the anesthetic to the 18-gauge needle and injecting the anesthetic into the area of the patient receiving treatment. Next, disconnecting the 10 ml syringe of the pair of 10 ml syringes from the 18-gauge needle. Then, connecting a plasma gel filled 10 ml syringe of the plurality of gel filled 10 ml syringes to the 18-gauge needle. Next, manipulating the 18-gauge needle in the direction of the directional lines and injecting the plasma gel of the plurality of plasma gel filled 10 ml syringes into the area of the patient receiving treatment, the injecting of the plasma gel into the area of the patient receiving treatment shall comprise of the repeated steps of connecting the plasma gel filled 10 ml syringe of the plurality of gel filled 10 ml syringes to the 18-gauge needle, injecting the plasma gel into the area of the patient receiving treatment, then disconnecting the plasma gel filled 10 ml syringe of the plurality of the gel filled 10 ml syringes from the 18-gauge needle until the area of the patient receiving treatment has been filled with the plasma gel determined to be sufficient by a medical practitioner to achieve augmentation. Then, removing the 18-gauge needle from the insertion point. And, lastly, placing a band-aid over the insertion point.

When performing the present method, no more than fifty 8.5 ml blood collection tubes shall be used to extract the blood from the patient.

In a preferred embodiment of the present invention, the 18-gauge needle of the present invention is only inserted and manipulated in the area of the patient receiving treatment that contains an adipose tissue.

The present invention requires that at least 340 ml of the blood is extracted from the patient and that no more than 425 ml of the blood is extracted from the patient.

The present invention requires that the patient's hemoglobin must be at least 12.5 to perform the augmentation.

The band-aid of the present invention, in preferred embodiments, is waterproof.

The 18-gauge needle used in the present invention is essential to properly inject the plasma gel into the adipose tissue of the patient receiving the augmentation.

In preferred embodiments of the present invention, the sterilizing solution will be one that is made using iodine and Chlorhexidine.

In a preferred embodiment, the centrifuge is a platelet-rich plasma centrifuge.

The marking of an area to be treated is an essential step of this invention, for the marking will ensure that only one insertion point is made for each area that is to receive augmentation.

The present invention, for the sake of brevity can be described as follows: A method of performing a buttocks and hip augmentation using plasma gel, the method comprises the steps of first, extracting at least 340 ml of blood from a patient. Then, separating the liquid plasma from the blood of the patient. Next, transforming the liquid blood into a plasma gel. Then, marking area of the buttocks and hips of the patient that will receive an injection that contains the plasma gel for augmentation, the area that receives the injection is referred as the injection point. Next, injecting the plasma gel into the area of the buttocks and hips that are to be augmented of the patient until augmentation is reached. And, lastly, covering the injection point that was used to create the augmentation.

An advantage of the present invention is that it provides a method that uses one's own plasma to augment one's own buttocks and hip.

Another advantage of the present invention is that it uses a minimal amount of blood collection tubes when performing a plasma gel buttocks and hip augmentation.

Yet another advantage of the present invention is that it reduces the time needed to collect blood and transform the blood into a plasma gel that is used to perform a plasma gel buttocks and hip augmentation.

Still another advantage of the present invention is that it eliminates the use of a girdle that a patient normally wears when a buttocks or hip augmentation is made.

While the inventor's description contains many specificities, these should not be construed as limitations of the method of performing a buttocks and hip augmentation using plasma gel but rather as an exemplification of several preferred embodiments thereof; any other variations may be possible. Accordingly, the scope should be determined not by the embodiments illustrated, but by the specification, the drawings, and the claims and any legal equivalent thereof.

What is claimed is:

1. A method of performing a buttocks and hip augmentation using plasma gel, the method comprises:

providing at least thirty-six 8.5 ml blood collection tubes;

providing a 21-gauge butterfly needle;

providing a plurality of 10 ml syringes and a plurality of caps for the plurality of 10 ml syringes;

providing a centrifuge;

providing a heating machine that is configured to receive the plurality of 10 ml syringes;

providing a container that holds cold water;

providing a pair of 10 ml syringes, the pair of 10 ml syringes are filled with 6 ml of a solution that comprises of a lidocaine and of a 2 percent epinephrine, the solution hereinafter shall be referred as an anesthetic;

providing an 18-gauge needle;

providing a marker that is configured to mark an area of a patient wherein a plasma gel will be injected;

providing a sterilizing solution that is used to sterilize a skin of the patient that will receive a treatment;

providing a disposable sterilized undergarment that will not cover an area of the patient that will receive the treatment;

providing a band-aid;

providing the patient;

providing a bed wherein the patient shall rest;

extracting blood from the patient into the at least thirty-six 8.5 ml blood collection tubes using the 21-gauge butterfly needle, thereby creating at least thirty-six blood filled collection tubes;

placing the at least thirty-six blood filled collection tubes into the centrifuge for a period of at least ten minutes;

extracting from the at least thirty-six blood filled collection tubes a liquid plasma using the plurality of 10 ml syringes and capping the syringes with the plurality of caps, thereby creating a plurality of liquid plasma filled and capped 10 ml syringes;

then, placing the plurality of liquid plasma filled and capped 10 ml syringes into a platelet rich plasma heating machine for at least 3 minutes, therefore transforming the liquid plasma into a plasma gel, and thereby creating a plurality of plasma gel filled 10 ml syringes;

next, cooling the plasma gel of the plurality of plasma gel filled 10 ml syringes in the container that holds the cold water for a period of at least 5 minutes;

then, instructing the patient to put on the disposable sterilized undergarment;

next, having the patient rest on the bed so that the area of the patient that will receive a treatment is exposed, the area of the patient that will receive treatment shall either be a buttocks or a hip of the patient;

then, marking with the marker the area of the patient wherein the 18-gauge needle will be inserted, the marking shall comprise of a plurality of directional lines that will flow outward from an insertion point, the directional lines are configured to be used as guides as to the direction in which the plasma gel is to be injected;

then, sterilizing the area of the patient that will receive treatment with a sterilizing solution;

next, inserting the 18-gauge needle into the insertion point;

then, connecting a 10 ml syringe of the pair of 10 ml syringes that contain the anesthetic to the 18-gauge needle and injecting the anesthetic into the area of the patient receiving treatment;

next, disconnecting the 10 ml syringe of the pair of 10 ml syringes from the 18-gauge needle;

then, connecting a plasma gel filled 10 ml syringe of the plurality of gel filled 10 ml syringes to the 18-gauge needle;

next, manipulating the 18-gauge needle in the direction of the directional lines and injecting the plasma gel of the plurality of plasma gel filled 10 ml syringes into the area of the patient receiving treatment, the injecting of the plasma gel into the area of the patient receiving treatment shall comprise of the repeated steps of connecting the plasma gel filled 10 ml syringe of the plurality of gel filled 10 ml syringes to the 18-gauge needle, injecting the plasma gel into the area of the patient receiving treatment, then disconnecting the plasma gel filled 10 ml syringe of the plurality of the gel filled 10 ml syringes from the 18-gauge needle until the area of the patient receiving treatment has been filled with the plasma gel determined to be sufficient by a medical practitioner to achieve augmentation;

then, removing the 18-gauge needle from the insertion point; and lastly, placing band-aid over the insertion point.

2. The method of performing the buttocks and hip augmentation using plasma gel of claim 1, wherein no more than fifty 8.5 ml blood collection tubes shall be used to extract the blood from the patient.

3. The method of performing the buttocks and hip augmentation using plasma gel of claim 2, wherein the 18-gauge needle is inserted and manipulated in the area of the patient receiving treatment that contains an adipose tissue.

4. The method of performing the buttocks and hip augmentation using plasma gel of claim 1, wherein at least 340 ml of the blood is extracted from the patient.

5. The method of performing the buttocks and hip augmentation using plasma gel of claim 1, wherein at most 425 ml of the blood is extracted from the patient.

6. The method of performing the buttocks and hip augmentation using plasma gel of claim 1, wherein the patient's hemoglobin must be at least 12.5 to perform the augmentation.

7. The method of performing the buttocks and hip augmentation using plasma gel of claim 1, wherein the centrifuge is a platelet-rich plasma centrifuge.

8. A method of performing a buttocks and hip augmentation using plasma gel, the method comprises the steps of:

first, extracting at least 340 ml of blood from a patient;

then, separating the liquid plasma from the blood of the patient;

next, transforming the liquid blood into a plasma gel;

then, marking an area of the buttocks and hips of the patient that will receive an injection that contains the plasma gel for augmentation, the area that receives the injection is referred as the injection point;

next, injecting the plasma gel into the area of the buttocks and hips that are to be augmented of the patient until augmentation is reached; and lastly, covering the injection point that was used to create the augmentation.

* * * * *